United States Patent
Ward et al.

(10) Patent No.: US 9,320,857 B2
(45) Date of Patent: Apr. 26, 2016

(54) NEEDLE SAFETY DEVICE

(71) Applicant: SANOFI-AVENTIS DEUTSCHLAND GMBH, Frankfurt am Main (DE)

(72) Inventors: Chris Ward, Prestatyn (GB); John Slemmen, Merseyside (GB)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 43 days.

(21) Appl. No.: 14/346,384

(22) PCT Filed: Sep. 20, 2012

(86) PCT No.: PCT/EP2012/068568
§ 371 (c)(1),
(2) Date: Mar. 21, 2014

(87) PCT Pub. No.: WO2013/041639
PCT Pub. Date: Mar. 28, 2013

(65) Prior Publication Data
US 2014/0221937 A1    Aug. 7, 2014

(30) Foreign Application Priority Data
Sep. 23, 2011   (EP) ................................. 11182627

(51) Int. Cl.
*A61M 5/32*   (2006.01)

(52) U.S. Cl.
CPC ........... *A61M 5/3257* (2013.01); *A61M 5/3243* (2013.01); *A61M 5/3271* (2013.01); *A61M 2005/3258* (2013.01)

(58) Field of Classification Search
CPC .............. A61M 2005/3247; A61M 2005/325; A61M 5/3273; A61M 2005/3254; A61M 25/0618
USPC ........................................ 604/197, 198, 263
See application file for complete search history.

(56) References Cited

U.S. PATENT DOCUMENTS

| | | | | |
|---|---|---|---|---|
| 2002/0193745 A1* | 12/2002 | Ferguson | ........................ | 604/192 |
| 2002/0193748 A1* | 12/2002 | Cocker et al. | ................. | 604/198 |
| 2003/0060776 A1* | 3/2003 | Heiniger | ........................ | 604/198 |
| 2003/0181875 A1* | 9/2003 | Bressler et al. | ............... | 604/263 |

(Continued)

FOREIGN PATENT DOCUMENTS

| | | |
|---|---|---|
| WO | 02/20074 | 3/2002 |
| WO | 03/066141 | 8/2003 |
| WO | 2008/077706 | 7/2008 |

OTHER PUBLICATIONS

International Search Report for Int. App. No. PCT/EP2012/068568, completed Apr. 4, 2013.

*Primary Examiner* — Gerald Landry, II
(74) *Attorney, Agent, or Firm* — Fish & Richardson P.C.

(57) ABSTRACT

Described is a needle safety device comprising a needle hub adapted to couple to an injection device a needle coupled to the needle hub and having a distal tip, a needle shield telescopically coupled to the needle hub and including a biasing element, and a locking element arranged on the needle hub. When the needle shield is in a first axial position, the needle shield covers the distal tip of the needle. When the needle shield is in a second axial position, the needle shield moves proximally relative to the needle hub to expose the distal tip of the needle and the locking element deflects the biasing element. When the needle shield is in a third axial position, the locking element engages the biasing element and the needle shield covers the distal tip of the needle.

9 Claims, 2 Drawing Sheets

(56) References Cited

U.S. PATENT DOCUMENTS

| | | | |
|---|---|---|---|
| 2004/0143195 A1* | 7/2004 | Bressler | A61M 25/0625 600/573 |
| 2007/0038185 A1* | 2/2007 | Albert et al. | 604/164.08 |
| 2009/0005737 A1* | 1/2009 | Chun | A61M 5/2033 604/157 |
| 2009/0157011 A1* | 6/2009 | Sansoucy et al. | 604/195 |
| 2009/0157013 A1* | 6/2009 | Wong | 604/263 |
| 2009/0216201 A1* | 8/2009 | Meehan et al. | 604/263 |
| 2010/0036326 A1* | 2/2010 | Matusch | 604/198 |
| 2011/0288491 A1* | 11/2011 | Newman | A61M 5/326 604/198 |
| 2012/0101475 A1* | 4/2012 | Wilmot | A61M 5/2033 604/506 |
| 2013/0030376 A1* | 1/2013 | Doyle | A61M 5/326 604/198 |
| 2013/0274671 A1* | 10/2013 | Jennings | A61M 5/20 604/154 |

* cited by examiner

NEEDLE SAFETY DEVICE

CROSS REFERENCE TO RELATED APPLICATIONS

The present application is a U.S. National Phase Application pursuant to 35 U.S.C. §371 of International Application No. PCT/EP2012/068568 filed Sep. 20, 2012, which claims priority to European Patent Application No. 11182627.7 filed Sep. 23, 2011. The entire disclosure contents of these applications are herewith incorporated by reference into the present application.

TECHNICAL FIELD

This invention relates to safety needle devices that cover a used needle after use.

BACKGROUND

Medicament delivery devices (e.g., pen injectors, syringes, auto-injectors, etc.) that contain a selected dosage of a medicament are well known devices for administering the medicament to a patient. Safety devices for covering a needle of the delivery device before and after use are also well known. Typically, a needle shield of the safety device is either manually moved or automatically to surround the medical needle. Various attempts have been made to develop an optimally sized and functioning safety device. However, there remains a need for an optimal safety needle assembly.

SUMMARY

It is an object of the present invention to provide an improved safety needle assembly that minimizes the risk of an accidental needle stick injury, that is safe to handle, and that provides needle safety before and after the medicament is delivered.

In an exemplary embodiment, a needle safety device comprises a needle hub adapted to couple to an injection device, a needle coupled to the needle hub and having a distal tip, a needle shield telescopically coupled to the needle hub and including a biasing element, and a locking element arranged on the needle hub. When the needle shield is in a first axial position, the needle shield covers the distal tip of the needle. When the needle shield is in a second axial position, the needle shield moves proximally relative to the needle hub to expose the distal tip of the needle and the locking element deflects the biasing element. When the needle shield is in a third axial position, the locking element engages the biasing element and the needle shield covers the distal tip of the needle.

In an exemplary embodiment, the needle hub includes a mounting element for coupling to the injection device. The mounting element includes an inner wall adapted to engage the injection device and an outer wall, with a slot formed between the inner wall and the outer wall. A proximal end of the needle shield is contained in the slot. A compression spring is disposed in the slot.

In an exemplary embodiment, the locking element includes an arm and a locking tab. The biasing element includes a resilient beam extending axially within the needle shield. The resilient beam includes a locking recess adapted to engage the locking tab. A proximal end of the resilient beam includes a pocket adapted to engage the locking tab to prevent proximal movement of the needle shield relative to the needle hub when the needle shield is in the third axial position.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
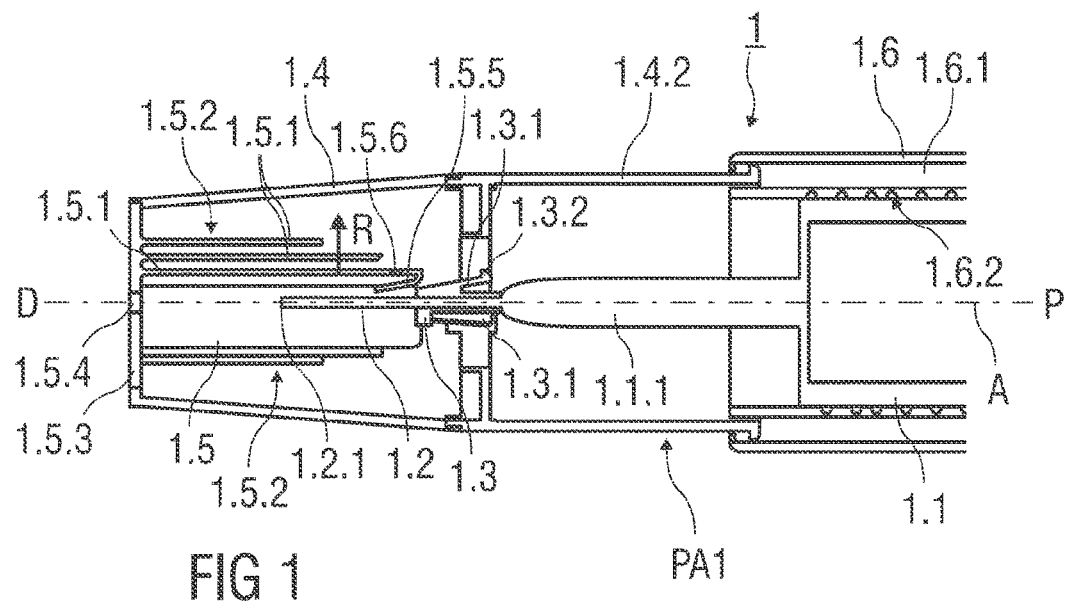
FIG. 1 shows a sectional view of an exemplary embodiment of a needle safety device with a needle shield positioned in a first axial position.

FIG. 1 shows sectional view of an exemplary embodiment of a needle safety device 1 in a first axial position (PA1), which may correspond to a pre-use condition. The safety device 1 comprises a needle hub 1.1 adapted to couple to an injection device (e.g., a syringe, a pen injector, an auto-injector, etc.), a needle 1.2 coupled to the needle hub 1.1, a locking element 1.3, a needle shield 1.4 telescopically coupled to the needle hub 1.1, and a biasing element 1.5.

In an exemplary embodiment, the needle hub 1.1 includes a proximal portion adapted to couple to an injection device, e.g., a syringe, a pen injector, an auto-injector, etc. For example, the proximal portion may include threads, a bayonet fit, a snap-fit arrangement, a friction-fit arrangement, etc. for coupling to the injection device. In an exemplary embodiment, the proximal portion may include a mounting element 1.6 having an inner wall 1.6.2 with a threaded surface adapted to engage threads on the injection device and an outer wall 1.6.1) spaced radially from the inner wall 1.6.2. As explained further below, a slot formed between the inner and outer walls 1.6.2, 1.6.1 may allow the needle shield 1.4 to translate axially relative to the needle hub 1.1.

Extending distally from the needle hub 1.1 may be a stem 1.1.1 which holds the needle 1.2. A distal tip 1.2.1 of the needle 1.2 extends distally from the stem 1.1.1, and a proximal tip of the needle 1.2 extends proximally from the stem 1.1.1 and is adapted to pierce a septum on a container of medicament when the safety device 1 is coupled to the injection device.

In an exemplary embodiment, a locking element 1.3 is arranged on a distal portion of the stem 1.1.1. The locking element 1.3 includes a arm 1.3.1 having a locking tab 1.3.2 at its proximal end. The arm 1.3.1 may extend radially away from a longitudinal axis A of the safety device 1. In another exemplary embodiment, the locking element 13 may be coupled to the needle 1.2.

Figure 2:
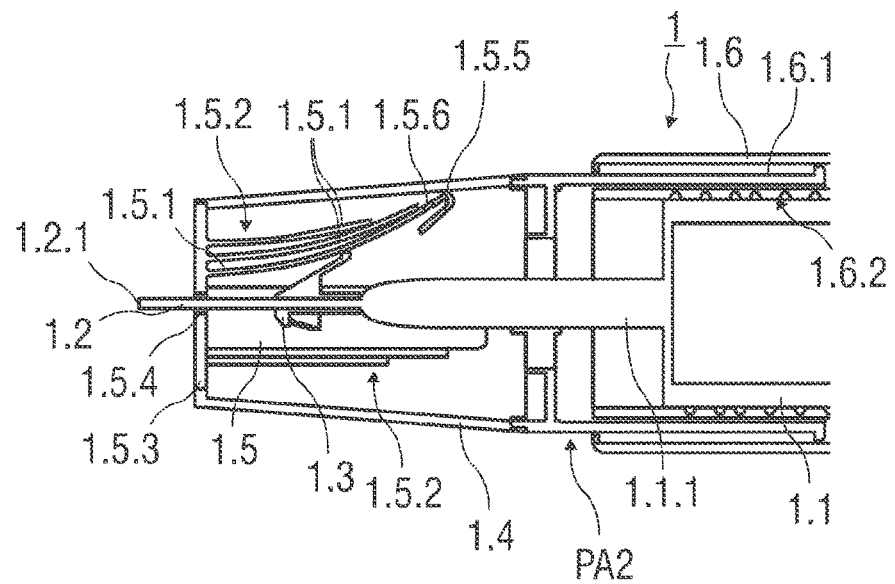
FIG. 2 shows a sectional view of an exemplary embodiment of a needle safety device with a needle shield positioned in a second axial position.
Figure 3:
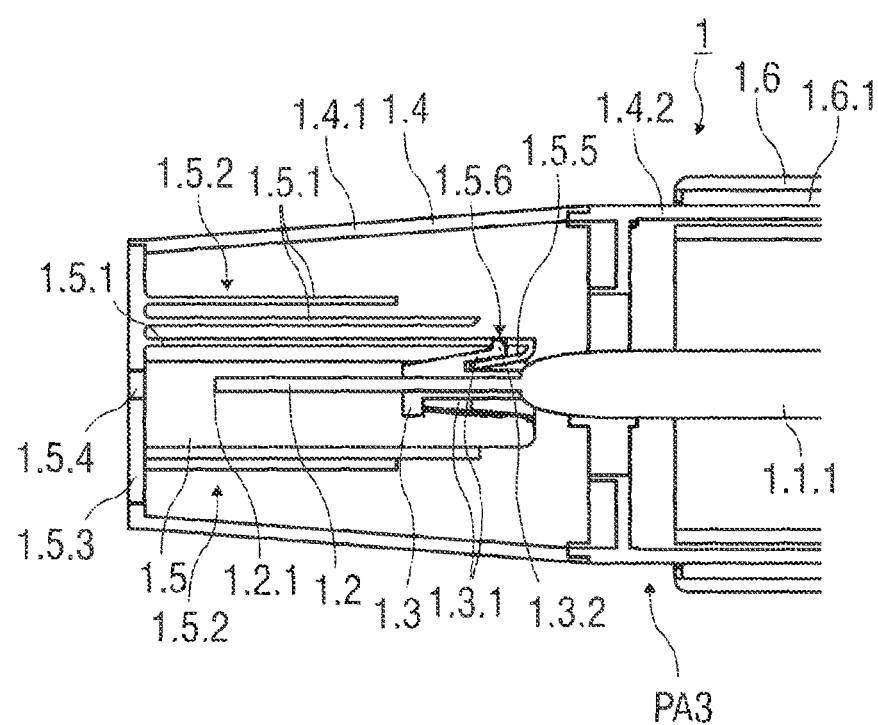
FIG. 3 shows a sectional view of an exemplary embodiment of a needle safety device with a needle shield positioned in a third axial position.

The needle shield 1.4 may move between an extended position (the first axial position (PA1) shown in FIG. 1), a retracted position (a second axial position (PA2) shown in FIG. 2, and an extended, locked position (a third axial position (PA3) shown in FIG. 3). A proximal end of the needle shield 1.4 may be housed with the slot of the needle hub 1.1. A flanged formed on the proximal end of the needle shield 1.4 may abut a corresponding flange formed on a distal end of the needle hub 1.1 to prevent the needle shield 1.4 from separating from the needle hub 1.1. In an exemplary embodiment, a spring element may reside in the slot and bias the needle shield 1.4 in the first axial position (PA1).

The needle shield 1.4 may include a middle portion 1.4.1 extending distally from the proximal portion, and a distal portion 1.4.2 extending distally from the middle portion 1.4.1. In use, the distal portion 1.4.2 covers the distal tip 1.2.1 of the needle 1.2 when the needle shield 1.4 is in the first and third axial positions (PA1, PA3). The middle and distal portions 1.4.1, 1.4.2 may be conical, frusto-conical, cylindridcal, or any other shape. The needle shield 1.4 may include a distal face 1.5.3 which is pressed against an injection site when an injection is to be administered. The distal face 1.5.3 may include an aperture (1.5.4) for allowing the needle 1.2 to pass through during the injection procedure.

In an exemplary embodiment, the biasing element 1.5 is coupled to the distal portion 1.4.2 of the needle shield 1.4. In the exemplary embodiment shown in FIG. 1, the biasing element 1.5 includes one or more resilient beams 1.5.1 (e.g., leaf springs) extending axially in a proximal direction from a proximal surface of the distal face 1.5.3 of the needle shield 1.4. In an exemplary embodiment, a spring assembly 1.5.2 may be formed by arranging a series of the resilient beams 1.5.1 in a radial fashion with a longest beam closest to the axis A and a shortest beam furthest from the axis A. In other exemplary embodiments, the biasing element 15 may be concentric spring elements.

In an exemplary embodiment, the resilient beam 1.5.1 closest to the axis A includes a ramped portion and a locking recess 1.5.6 formed on its proximal end. As explained further below, the ramped portion engages the arm 1.3.1 when the needle shield 1.4 moves from the first axial position (PA1) to the second axial position (PA2), and the locking recess 1.5.6 engages the locking tab 1.3.2 when the needle shield 1.4 is in the third axial position (PA3).

A peelable film (not shown) may be placed on the distal face 1.5.3 of the needle shield 1.4 to maintain sterility of the needle 1.2 prior to use.

In FIG. 1, the needle shield 1.4 is in the first axial position (PA1) relative to the needle hub 1.1.

As shown in FIG. 2, when the needle shield 1.4 is pressed against the injection site, the needle shield 1.4 moves proximally relative to the needle hub 1.1 from the first axial position (PA1) to the second axial position (PA2). As the needle shield 1.4 moves from the first axial position (PA1) to the second axial position (PA2), the arm 1.3.1 deflects the resilient beams 1.5.1. For example, the arm 1.3.1 may first engage the ramped portion of the proximal end of the resilient beam 1.5.1, causing the resilient beam 1.5.1 to deflect radially. The deflected resilient beam 1.5.1 may abut other resilient beams causing the other resilient beams to deflect radially. When the needle shield 1.4 is in the second axial position (PA2), the distal tip 1.2.1 of the needle 1.2 is exposed (and presumably has pierced the injection site).

As shown in FIG. 3, as force is removed from the needle shield 1.4 (e.g., when the needle safety device 1 is being removed from the injection site), force stored in the resilient beams 1.5.1 (due to the deflection) is applied to the locking element 1.3 which moves the needle shield 1.4 from the second axial position (PA2) into the third axial position (PA3). During this movement, the locking tab 1.3.2 may ride along a surface of the deflected resilient beam 1.5.1. When the locking tab 1.3.2 reaches the locking recess 1.5.6 formed in the deflected resilient beam 1.5.1, the needle shield 1.4 is prevented from moving relative to the needle hub 1.1. Any further movement of the needle shield 1.4 in the proximal direction is prevented by an engagement of the locking tab 1.3.2 in a pocket 1.5.5 formed by the ramped end of the proximal end of the resilient beam 1.5.1. Thus, in the third axial position (PA3) the safety device 1 is needle-safe, such that the distal tip 1.2.1 of the needle 1.2 will not be exposed if force is applied to the needle shield 1.4.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle safety device comprising:
   a needle hub adapted to couple to an injection device;
   a needle coupled to the needle hub, the needle having a distal tip;
   a needle shield telescopically coupled to the needle hub with a biasing element coupled to a distal portion of the needle shield; and
   a locking element arranged on the needle hub,
   wherein, when the needle shield is in a first axial position, the needle shield covers the distal tip of the needle,
   wherein, when the needle shield is in a second axial position, the needle shield moves proximally relative to the needle hub to expose the distal tip of the needle and the locking element directly deflects the biasing element, and
   wherein, when the needle shield is in a third axial position, the locking element engages the biasing element and the needle shield covers the distal tip of the needle.

2. The needle safety device according to claim 1, wherein the needle hub includes a mounting element for coupling to the injection device.

3. The needle safety device according to claim 2, wherein the mounting element includes an inner wall adapted to engage the injection device and an outer wall, with a slot formed between the inner wall and the outer wall.

4. The needle safety device according to claim 3, wherein a proximal end of the needle shield is contained in the slot.

5. The needle safety device according to claim 4, wherein a compression spring is disposed in the slot.

6. The needle safety device according to claim 1, wherein the locking element includes an arm and a locking tab.

7. The needle safety device according to claim 6, wherein the biasing element includes a resilient beam extending axially within the needle shield.

8. The needle safety device according to claim 7, wherein the resilient beam includes a locking recess adapted to engage the locking tab.

9. The needle safety device according to claim 8, wherein a proximal end of the resilient beam includes a pocket adapted to engage the locking tab to prevent proximal movement of the needle shield relative to the needle hub when the needle shield is in the third axial position.

* * * * *